(12) United States Patent
Sakaguchi

(10) Patent No.: US 12,220,340 B2
(45) Date of Patent: Feb. 11, 2025

(54) NASAL DILATOR

(71) Applicant: Teruko Sakaguchi, Saitama (JP)

(72) Inventor: Teruko Sakaguchi, Saitama (JP)

( * ) Notice: Subject to any disclaimer, the term of this patent is extended or adjusted under 35 U.S.C. 154(b) by 0 days.

(21) Appl. No.: 18/257,087

(22) PCT Filed: Jul. 26, 2021

(86) PCT No.: PCT/JP2021/027514
§ 371 (c)(1),
(2) Date: Jun. 12, 2023

(87) PCT Pub. No.: WO2022/130673
PCT Pub. Date: Jun. 23, 2022

(65) Prior Publication Data
US 2024/0082042 A1  Mar. 14, 2024

(30) Foreign Application Priority Data
Dec. 14, 2020  (JP) .................. 2020-206944

(51) Int. Cl.
*A61F 5/08* (2006.01)

(52) U.S. Cl.
CPC ........ *A61F 5/08* (2013.01); *A61F 2210/0076* (2013.01)

(58) Field of Classification Search
CPC ............ A61F 5/08; A61F 13/126; A61F 2013/00476; A61F 2210/0076; A61B 17/085; A61B 5/6833; A45D 44/22
See application file for complete search history.

(56) References Cited

U.S. PATENT DOCUMENTS 5,842,469 A * 12/1998 Rapp .................. A61F 5/08
128/207.18
6,318,362 B1 * 11/2001 Johnson .............. A61F 13/0259
128/207.18
(Continued)

FOREIGN PATENT DOCUMENTS

CN  1370210 A  9/2002
CN  1623519 A  6/2005
(Continued)

OTHER PUBLICATIONS

International Search Report and Written Opinion for PCT/JP201/027514 (Nov. 5, 2021).
(Continued)

*Primary Examiner* — Majid Jamialahmadi
(74) *Attorney, Agent, or Firm* — Holzer Patel Drennan

(57) ABSTRACT

This invention relates to a nasal dilator. An object of this invention is to provide a nasal dilator wherein adhesive substance layer is prevented from adhering to a top region of a nose bridge, and which does not need a dedicated member for preventing the adhesion of the substance layer to the top region of the nose bridge. The object is achieved by a nasal dilator comprising a flexible strip, an adhesive substance layer formed on one surface of the flexible strip and a release liner covering the adhesive substance layer, wherein the adhesive substance layer is formed on entire surface of said one surface of the flexible strip, the release liner is divided into three pieces, a first of which covers one longitudinal end region of the adhesive substance layer, a second of which covers longitudinal middle region of the adhesive substance layer and a third of which covers another longitudinal end region of the adhesive substance layer.

3 Claims, 1 Drawing Sheet

(56) References Cited

U.S. PATENT DOCUMENTS

| | | | |
|---|---|---|---|
| 6,676,681 B1 * | 1/2004 | Blach | A61F 5/08 |
| | | | 606/199 |
| 2010/0228282 A1 | 9/2010 | Fenton | |
| 2017/0057197 A1 | 3/2017 | Arbesman | |
| 2018/0360584 A1 * | 12/2018 | Chiapetta | A01K 29/00 |

FOREIGN PATENT DOCUMENTS

| | | |
|---|---|---|
| EP | 1006963 B1 | 4/2004 |
| JP | 2005-087766 A | 4/2005 |
| JP | 2005-87766 A | 4/2005 |
| JP | 2014-073210 A | 4/2014 |
| WO | 2017/130838 A1 | 8/2017 |

OTHER PUBLICATIONS

International Preliminary Report on Patentability for PCT/JP201/027514 (Jan. 10, 2022).

* cited by examiner

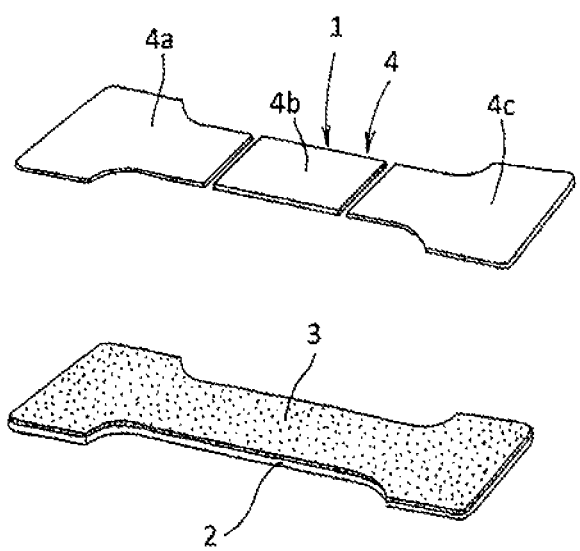

NASAL DILATOR

CROSS-REFERENCE TO RELATED APPLICATIONS

This application is a National Stage application of PCT/JP2021/027514, filed Jul. 26, 2021, which claims priority to Japanese Patent Application No. 2020-206944, filed Dec. 14, 2020, which applications are incorporated herein by reference. To the extent appropriate, a claim of priority is made to each of the above disclosed applications.

TECHNICAL FIELD

This invention relates to a nasal dilator.

BACKGROUND ART

Patent literature 1 discloses a nasal dilator comprising a flexible strip, an adhesive substance layer formed on one surface of the flexible strip and a release liner divided into two pieces and covering the adhesive substance layer. When the nasal dilator is used, both pieces of the release liner are removed from the adhesive substance layer, and then the adhesive substance layer is adhered to the nose bridge.

In the nasal dilator of Patent literature 1, a pad or a net is adhered to a longitudinal middle region of the adhesive substance layer so as to prevent adhesion of the adhesive substance layer to a top region of the nose bridge, thereby preventing peeling of skin of the top region of the nose bridge and damage of the top region of the nose bridge at the time of removal of the nasal dilator from the nose bridge.

CITATION LIST

Patent Literature

PTL 1: Japanese Patent Laid-Open No. 2005-087766

SUMMARY OF INVENTION

Technical Problem

The nasal dilator of PTL 1 has a disadvantage in that it needs a dedicated member, i.e. a pad or net, for preventing adhesion of the adhesive substance layer to the top region of the nose bridge.

Therefore, an object of this invention is to provide a nasal dilator comprising a flexible strip, an adhesive substance layer formed on one surface of the flexible strip and a release liner covering the adhesive substance layer, which is used with the release liner removed from the adhesive substance layer, the adhesive substance layer adhered to the nose bridge and the adhesive substance layer prevented from adhering to a top region of the nose bridge, and which does not need a dedicated member for preventing adhesion of the adhesive substance layer to the top region of the nose bridge.

Solution to Problem

In accordance with this invention, there is provided a nasal dilator comprising a flexible strip, an adhesive substance layer formed on entire of one surface of the flexible strip and a release liner covering the adhesive substance layer, characterized in that the release liner is divided into a first piece covering one longitudinal end region of the adhesive substance layer and removed from the adhesive substance layer at the time of use of the nasal dilator, a second piece covering longitudinal middle region of the adhesive substance layer and left adhering to the longitudinal middle region of the adhesive substance layer at the time of use of the nasal dilator and a third piece covering another longitudinal end region of the adhesive substance layer and removed from the adhesive substance layer at the time of use of the nasal dilator.

Advantageous Effects of Invention

When the nasal dilator is used with both of the longitudinal end pieces, i.e. the first and the third pieces, of the release liner removed from the adhesive substance layer and the longitudinal middle piece, i.e. the second piece, of the release liner left adhering to the adhesive substance layer, the longitudinal middle piece of the release liner abuts the top region of the nose bridge and the adhesive substance layer does not adhere to the top region of the nose bridge. Therefore, the adhesive substance layer does not peel skin of the top region of the nose bridge and the top region of the nose bridge is not damaged when the nasal dilator is removed from the nose bridge. It suffices to divide the release liner into three pieces and no dedicated member is necessary for preventing adhesion of the adhesive substance layer to the top region of the nose bridge.

BRIEF DESCRIPTION OF DRAWINGS

FIG. 1 is an exploded perspective view of a nasal dilator in accordance with a preferred embodiment of this invention.

DESCRIPTION OF EMBODIMENTS

As shown in FIG. 1, a nasal dilator 1 in accordance with a preferred embodiment comprises a flexible strip 2, an adhesive substance layer 3 formed on one surface of the flexible strip 2 and a release liner 4 adhering to and covering the adhesive substance layer 3. The flexible strip 2 is a single or composite material member made of paper, cloth, plastic or the like. The release liner 4 is made of paper, plastic, or the like. The adhesive substance layer 3 is formed on entire surface of said one surface of the flexible strip 2. The release liner 4 is divided into three pieces, namely, a first piece 4a covering one longitudinal end region of the adhesive substance layer 3, a second piece 4b covering longitudinal middle region of the adhesive substance layer 3 and a third piece 4c covering another longitudinal end region of the adhesive substance layer 3.

When the nasal dilator 1 is used, the first piece 4a and the third piece 4c of the release liner 4 are removed from the adhesive substance layer 3, the second piece 4b of the release liner 4, which is left adhering to the longitudinal middle region of the adhesive substance layer 3, is abutted on a top region of the nose bridge, and the two longitudinal end regions of the adhesive substance layer 3 are adhered to opposite side regions of the nose bridge. Restoring force of the flexible strip 2 bent along the nose bridge lifts the opposite side regions of the nose bridge to which the two longitudinal end regions of the adhesive substance layer 3 are adhered. Thus, the nasal cavity is expanded so as to relieve nasal blockage.

When the first piece 4a and the third piece 4c of the release liner 4 are removed from the adhesive substance layer 3 and the second piece 41) of the release liner 4 is left adhering to the longitudinal middle region of the adhesive substance layer 3 during use of the nasal dilator 1, the longitudinal middle portion of the release liner 4, i.e. the second piece 4b of the release liner 4, abuts the top region of the nose bridge so that the adhesive substance layer 3 does not adhere to the top region of the nose bridge. Therefore, the adhesive substance layer 3 does not peel skin of the top region of the nose bridge and the top region of the nose bridge is not damaged when the nasal dilator 1 is removed from the nose bridge.

Opposite longitudinal end regions of the adhesive substance layer 3 adhere to opposite side regions of the nose bridge.

Therefore, the nasal dilator 1 can exhibit good performance, Dividing the release liner 4 into three pieces 4a. 413 and 4c suffices and no dedicated member is necessary for preventing adhesion of the adhesive substance layer 3 to the top region of the nose bridge.

INDUSTRIAL APPLICABILITY

This invention can be widely used for nasal dilators.

REFERENCE SIGNS LIST

1 Nasal dilator
2 Flexible strip
3 Adhesive substance layer
4 Release liner
4a First piece
4h Second piece
4e Third piece

The invention claimed is:

1. A nasal dilator having a first end and an opposite second end, the nasal dilator comprising a flexible strip extending continuously from the first end to the second end, an adhesive substance layer formed on entire of one surface of the flexible strip and a release liner adhered to and covering the adhesive substance layer, wherein the release liner is divided into a first piece covering one longitudinal end region of the adhesive substance layer, a second piece covering a longitudinal middle region of the adhesive substance layer and a third piece covering another longitudinal end region of the adhesive substance layer, wherein the first piece, the second piece and the third piece are positioned in series in a nonoverlapping manner, wherein the second piece laterally forms a single section from a top edge of the nasal dilator to a bottom edge of the nasal dilator, with each of the first piece, the second piece and the third piece having a lateral height from the top edge of the nasal dilator to the bottom edge of the nasal dilator, with the lateral height of the second piece less than the lateral height of the first piece and of the third piece, and a longitudinal length of the flexible strip greater than the lateral height of each of the first piece, the second piece, and the third piece, and
    wherein after the nasal dilator has been configured to be placed on a nose of a user, the first piece and the third piece of the release liner are removed from the adhesive substance layer and the second piece remains adhered to the adhesive substance layer.

2. A nasal dilator having a first end and an opposite second end, the nasal dilator comprising a flexible strip extending continuously from the first end to the second end, an adhesive substance layer formed on entire of one surface of the flexible strip and a release liner adhered to and covering the adhesive substance layer, wherein the release liner is divided into three pieces, a first piece covering one longitudinal end region of the adhesive substance layer, a second piece covering a longitudinal middle region of the adhesive substance layer, and a third piece covering another longitudinal end region of the adhesive substance layer, the second piece laterally forms a single section from a top edge of the second piece to a bottom edge of the second piece, wherein the first piece, the second piece and the third piece are positioned in series in a nonoverlapping manner,
    wherein a right part of a top edge of the first piece, the top edge of the second piece, and a left part of a top edge of the third piece are aligned in a straight line, with a right part of a bottom edge of the first piece, the bottom edge of the second piece, and a left part of a bottom edge of the third piece are aligned in a straight line, with the aligned top edges of the three pieces and the aligned bottom edges of the three pieces extending parallel with each other; and
    wherein after the nasal dilator has been configured to be placed on a nose of a user, the first piece and the third piece of the release liner are removed from the adhesive substance layer and the second piece remains adhered to the adhesive substance layer.

3. A method of applying a nasal dilator to a nose of a user, the nasal dilator having a first end and an opposite second end, the nasal dilator comprising a flexible strip extending continuously from the first end to the second end, an adhesive substance layer formed on entire of one surface of the flexible strip and a release liner adhered to and covering the adhesive substance layer, the release liner divided into a first piece covering one longitudinal end region of the adhesive substance layer, a second piece covering a longitudinal middle region of the adhesive substance layer continuously as a single piece from a top edge of the nasal dilator to a bottom edge of the nasal dilator, wherein the second piece laterally forms a single section, and a third piece covering another longitudinal end region of the adhesive substance layer, wherein the first piece, the second piece and the third piece are positioned in series in a nonoverlapping manner, with each of the first piece, the second piece and the third piece having a lateral height from the top edge of the nasal dilator to the bottom edge of the nasal dilator, with the lateral height of the second piece less than the lateral height of the first piece and of the third piece, and a longitudinal length of the flexible strip greater than the lateral height of each of the first piece, the second piece, and the third piece, the method comprising:
    removing the first piece exposing the adhesive substance layer;
    removing the third piece exposing the adhesive substance layer; and
    applying the nasal dilator to the nose with the second piece left adhering to the adhesive substance layer continuously from the top edge of the nasal dilator to the bottom edge of the nasal dilator.

* * * * *

UNITED STATES PATENT AND TRADEMARK OFFICE
CERTIFICATE OF CORRECTION

| | |
|---|---|
| PATENT NO. | : 12,220,340 B2 |
| APPLICATION NO. | : 18/257087 |
| DATED | : February 11, 2025 |
| INVENTOR(S) | : Teruko Sakaguchi |

Page 1 of 1

It is certified that error appears in the above-identified patent and that said Letters Patent is hereby corrected as shown below:

In the Specification

Column 2, Line 66:
"piece (41) of the release"
Should be changed to:
--piece (4b) of the release--

Column 3, Line 14:
"mance, Dividing the"
Should be changed to:
--mance. Dividing the--; and
"pieces 4a. 413"
Should be changed to:
--pieces 4a, 4b--

Column 3, Line 29:
"4h Second piece"
Should be changed to:
--4b Second piece--

Column 3, Line 30:
"4e Third piece"
Should be changed to:
--4c Third piece--

Signed and Sealed this
Sixth Day of May, 2025

Coke Morgan Stewart
*Acting Director of the United States Patent and Trademark Office*